(12) United States Patent
Sloan

(10) Patent No.: US 10,467,214 B1
(45) Date of Patent: *Nov. 5, 2019

(54) TAXONOMIC FINGERPRINTING

(71) Applicant: ALLSCRIPTS SOFTWARE, LLC, Chicago, IL (US)

(72) Inventor: John Sloan, Raleigh, NC (US)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/859,645

(22) Filed: Dec. 31, 2017

Related U.S. Application Data

(63) Continuation of application No. 14/587,410, filed on Dec. 31, 2014, now Pat. No. 9,953,043.

(60) Provisional application No. 61/943,374, filed on Feb. 22, 2014.

(51) Int. Cl.
| | | |
|---|---|---|
| *G06F 17/30* | (2006.01) | |
| *G06F 16/22* | (2019.01) | |
| *G16H 50/00* | (2018.01) | |
| *G06F 16/28* | (2019.01) | |

(52) U.S. Cl.
CPC ........ *G06F 16/2228* (2019.01); *G06F 16/284* (2019.01); *G16H 50/00* (2018.01)

(58) Field of Classification Search
None
See application file for complete search history.

(56) References Cited

U.S. PATENT DOCUMENTS

| | | | | |
|---|---|---|---|---|
| 8,756,076 B2* | 6/2014 | Griffin | ........... | G06Q 50/24 |
| | | | | 705/2 |
| 8,788,289 B2* | 7/2014 | Flanagan | ........... | G06Q 10/10 |
| | | | | 705/3 |
| 2002/0082868 A1* | 6/2002 | Pories | ........... | G06F 19/324 |
| | | | | 705/3 |
| 2008/0040150 A1* | 2/2008 | Kao | ........... | G06F 19/325 |
| | | | | 705/2 |
| 2017/0124269 A1* | 5/2017 | McNair | ........... | G06F 19/00 |

* cited by examiner

*Primary Examiner* — Debbie M Le
(74) *Attorney, Agent, or Firm* — Medley, Behrens & Lewis, LLC

(57) ABSTRACT

A method for matching an instance to exemplars within a system includes receiving a plurality of literature regarding medical subject matter; including the received plurality of literature related to the medical subject matter into a text artifact; indexing the artifact using encodings to derive an initial code signature; deriving association rules from the artifact seeded by the signature to obtain a list of terminology to code mappings; receiving extensions to each of the code mappings to augment the mappings with the received extensions; indexing the artifact using the received extensions to obtain an exemplar code signature for the certain subject matter; and storing the generated exemplars for matching and instance; receiving an instance and generating an instance code signature using the received extensions; matching the instance code signature to one or more exemplar code signatures.

17 Claims, 6 Drawing Sheets

TAXONOMIC FINGERPRINTING

CROSS-REFERENCE TO RELATED APPLICATION

The present application is a U.S. nonprovisional patent application of, and claims priority under 35 U.S.C. § 119(e) to, U.S. provisional patent application Ser. No. 61/943,374, filed Feb. 22, 2014, which provisional patent application is incorporated by reference herein.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention relates to a computing device. More specifically, the present invention relates to navigating within a software application.

Undiagnosed or misdiagnosed illness costs patients their health and negatively impact providers. Furthermore, innovations in new drugs and therapies require accurate and timely identification of cohorts for clinical trials. Despite attempts to address this by enriching electronic health record (EHR) systems with ever-widening varieties of structured data fields, there will always be crucial findings hidden inside the unstructured text narrative about each patient.

Not only are patients who suffer from rare diseases prone to un- or misdiagnosed illnesses, but also patients who suffer complex and chronic illnesses that occur too often. Knowledge encodings such as controlled vocabularies, taxonomies, and ontologies map verbiages to taxons (i.e., clinical codes). They were intended to unlock the power of the clinical narrative. Unfortunately, their evolution lags that of medical science with their partially-automated use confined to discharge billing.

Therefore, there exists a need for an improved method for accessing relevant information in a software application. This and other needs are addressed by one or more aspects of the present invention.

SUMMARY OF THE INVENTION

The present invention includes many aspects and features. Moreover, while many aspects and features relate to, and are described in, the context of healthcare applications, the present invention is not limited to use only in this context, as will become apparent from the following summaries and detailed descriptions of aspects, features, and one or more embodiments of the present invention.

Accordingly, one aspect of the present invention relates to a method for A method for matching instance to exemplars within a system, the method comprising receiving a plurality of literature regarding a certain subject matter, including the received plurality of literature related to the certain subject matter into a text artifact, indexing the artifact using encodings to derive an initial code signature, deriving association rules from the artifact seeded by the signature to obtain a list of terminology to code mappings, receiving extensions to each of the code mappings to augment the mappings with the received extensions, indexing the artifact using the received extensions to obtain an exemplar code signature for the certain subject matter, and storing the generated exemplars for matching and instance.

In a feature of this aspect, further comprising receiving an instance and generate an instance code signature using the received extensions, and matching the instance code signature to one or more exemplar code signatures.

Another aspect relates to a method for matching an instance to exemplars within a system. The method includes receiving a plurality of literature regarding a certain subject matter; including the received plurality of literature related to the certain subject matter into a text artifact; indexing the artifact using encodings to derive an initial code signature; deriving association rules from the artifact seeded by the signature to obtain a list of terminology to code mappings; receiving extensions to each of the code mappings to augment the mappings with the received extensions; indexing the artifact using the received extensions to obtain an exemplar code signature for the certain subject matter; and storing the generated exemplars for matching an instance.

In a feature of this aspect, the method further includes receiving an instance and generating an instance code signature using the received extensions.

Another aspect relates to a method for matching an instance to exemplars within a system. The method includes receiving a plurality of literature regarding medical subject matter; including the received plurality of literature related to the medical subject matter into a text artifact; indexing the artifact using encodings to derive an initial code signature; deriving association rules from the artifact seeded by the signature to obtain a list of terminology to code mappings; receiving extensions to each of the code mappings to augment the mappings with the received extensions; indexing the artifact using the received extensions to obtain an exemplar code signature for the certain subject matter; and storing the generated exemplars for matching and instance; receiving an instance and generating an instance code signature using the received extensions; matching the instance code signature to one or more exemplar code signatures.

In a feature of this aspect, exemplars most closely matching an instance are those that minimize the square root of the sum of an instance's Hits and Misses.

In one or more preferred implementations, Hits are the sum of products of numbers both of which are less than one. In one or more preferred implementations, Hits are rewarded with closeness. In one or more preferred implementations, Misses are penalized with distance. In one or more preferred implementations, instance signatures having more entries than usual are not penalized. In one or more preferred implementations, a Hit to Miss ratio measures diagnostic adequacy of an instance.

Another aspect relates to a method for matching an instance to exemplars within a system. The method includes receiving a plurality of literature regarding retail subject matter; including the received plurality of literature related to the retail subject matter into a text artifact; indexing the artifact using encodings to derive an initial code signature; deriving association rules from the artifact seeded by the signature to obtain a list of terminology to code mappings; receiving extensions to each of the code mappings to augment the mappings with the received extensions; indexing the artifact using the received extensions to obtain an exemplar code signature for the certain subject matter; and storing the generated exemplars for matching and instance; receiving an instance and generating an instance code signature using the received extensions; matching the instance code signature to one or more exemplar code signatures.

In addition to the aforementioned aspects and features of the present invention, it should be noted that the present invention further encompasses the various possible combinations and sub-combinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein.

DETAILED DESCRIPTION

Figure 1:
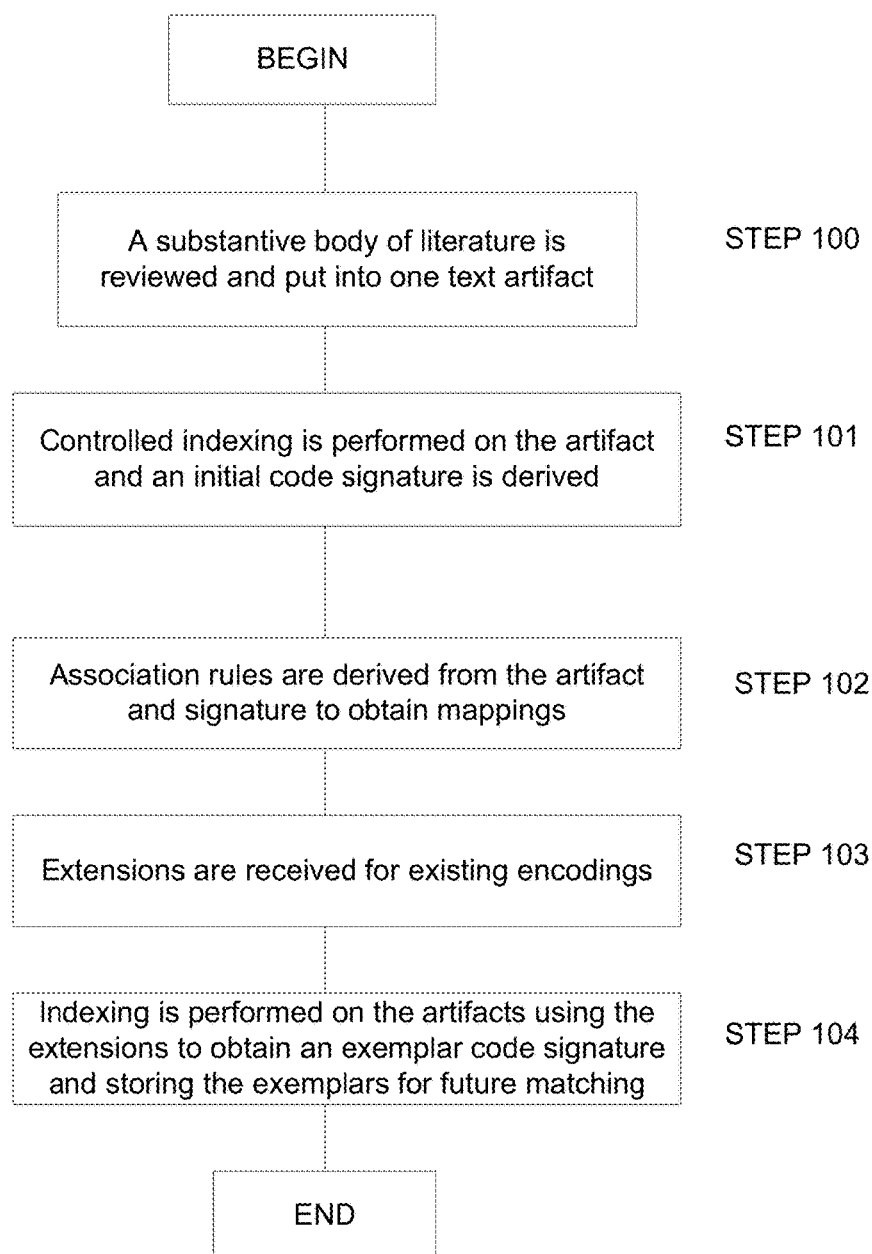
FIG. 1 is an example flow diagram of a method for generating one or more exemplars for matching with an instance in accordance with the present invention.

Referring now to the drawings, one or more preferred embodiments of the present invention are next described. The following description of one or more preferred embodiments is merely exemplary in nature and is in no way intended to limit the invention, its implementations, or uses.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

A computing device may be any type of device configured to operate and/or communicate in a wired and/or wireless environment. By way of example, the computing device may be configured to transmit and/or receive wireless signals. The computing device includes a memory for storing, for example, an interactive application, and a processor.

The interactive application (software) comprises a set of machine readable code stored on a machine readable medium and is executed by a processor included in the computing device. The application provides user interface tools in the form of graphical screen displays which allow the user to access information.

A disclosed implementation of a method for matching an instance with an exemplar borrows the fingerprinting metaphor from Forensic Science. In accordance with an example of this implementation this metaphor posits the patient as victim, the physician as detective, the presentation as crime scene, and disease as perpetrator. Fingerprinting includes acquiring a high quality exemplar print on each disease for future use. Later, prints acquired from patient presentation are matched to all exemplars, the closest matches are presented to the physician.

Figure 3:
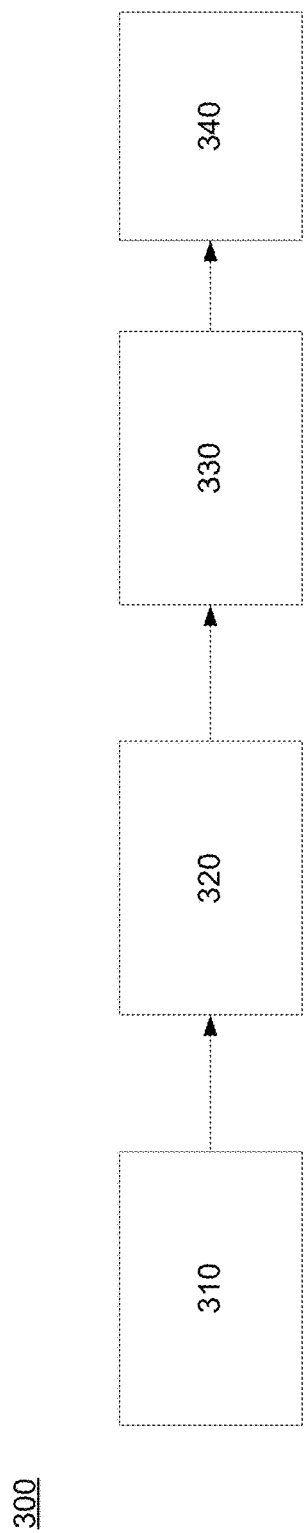
FIG. 3 is an example block diagram of a disclosed system configured to implement a method for generating one or more exemplars and matching an instance with one or more of the generated exemplars in accordance with the present invention.

Accordingly, a system is disclosed that is configured to implement the method for generating one or more exemplars and matching an instance with one or more of the generated exemplars. A block diagram of the disclosed system 300 is illustrated in FIG. 3. The system comprises an artifact engine 310, a signature generator 320, a mapping generator 330, an exemplar generator 340 and a matching processor 350.

An example flow diagram of an implementation of the disclosed method is illustrated in FIG. 1. In accordance with an implementation of the method, the artifact engine crawls an authoritative source of subject matter literature for admissible articles concerning a particular subject. STEP 100. For example, the artifact engine 310 may crawl PubMed or other authoritative source of medical literature for a particular disease. In this implementation, an article is admissible if it concerns the specific subject, e.g., disease (i.e., Relevance), the whole disease (i.e., Comprehensiveness), and nothing but the disease (i.e., Purity). The artifact engine 110 automatically determines the admissibility of an article. The determination includes controlled indexing of the article's metadata and then its content using all-encompassing clinical taxonomies, for example SNOMED, MeSH, or ICD-10. Building a large artifact while enforcing admissibility criteria reduces bias from imbalanced editorial emphasis. The size of an article's excerpt for inclusion into the artifact could also be made proportional to the journal's impact factor. This removes the "All voices are of equal importance" bias. Additional bibliometrics may also be applied to remove additional sources of bias.

The relevance is established by matching up top-ranked STEJCP entries indexed from the metadata in PubMed and those indexed from the body of the article. Articles that fail to matchup likely have their clinical taxonomies, e.g., MeSH terms, appear in the metadata, however the MeSH terms (or their ICD-10 approximations) are not mentioned in the body of the article. In these instances, the subject matter relative to its MeSH terms are merely implied, and therefore fail the relevance condition.

Comprehensiveness is established by the breath of codes appearing in the code signature. Articles failing this criteria might confine ICD-10 Verbiage to that disease's MeSH terms inside its abstract or introduction. Therefore, more comprehensive treatment of signs, symptoms, complications, are missing from the article. Most often, such otherwise sound and informative articles focus on the treatment of a disease, without lending the insight we need into that disease's pathophysiology. A comprehensive article in accordance with the implementation emphasizes pathophysiology (including signs, symptoms, etiologies, and diagnoses) over treatment.

Purity is measured by how tightly an article's Taxons cluster as compared to existing clusterings of clinical concepts. Articles failing this criteria have code signatures that span a wider subject matter than the disease under study. For example, due to its breadth, an article on type II diabetes mellitus will fail the purity condition for diabetic retinopathy—a particular complication of diabetes. Also, articles failing the Purity criteria may be comprised of deprecated or over-used terminologies of vague or low discriminatory power. Such articles cluster to a level of abstraction higher than SNOMED, MeSH, or ICD-10. These types of articles typically appear in online patient diaries and in some elementary patient education material. Articles satisfying all three admissibility criteria concerning a specific disease are concatenated into one large text artifact by the artifact engine.

The signature generator 320 then performs controlled indexing on the artifact from the artifact engine using a variety of encodings to derive an initial code signature. STEP 101. A controlled indexer front-ends a Boolean Valuator with a text preprocessor and back-ends it with a postprocessor in the signature generator. The preprocessor performs text boundary detection, tokenization, tagging, and related operations well-known in the art. Execution of the aaluator is controlled by an encoding derived from a forest of sum-of-products boolean expressions. Each expression maps one or more word combinations or verbiages to a clinical code or taxon. The post-processor is a machine learner that refines results of the valuator based on compiled hindsight (e.g., Bayesian reasoning).

Indexers equipped with text parsers are known by many names including "text inference engines", "NLP engines", or "Encoders", and "Named Entity Recognizers". Indexers are used in applications ranging from computer assisted (medical) coding to fault tree analysis.

As a text mining process, the preferred implementation compiles these expressions into a mathematical structure known as a hypergraph. In particular, this hypergraph is expressed as a collection of partial-order sets or posets. It mines taxons from this clause-term hypergraph using a match-count algorithm for each collection of words inside a unit of text narrative like a sentence or paragraph.

In the preferred implementation, the controlled indexer outputs a poset comprised of columns with acronym 'STEJCP'. Score S is actually a distance as described earlier. Ending displacement T and length E locate the sentence inside the document where the verbiage was detected. Displacement J locates the verbiage comprising the clause inside the Encoding. Finally, taxon or class label C associated with the detected verbiage P comprise the final two columns. Various applications of the controlled indexer may use different subsets of columns. The preferred implementation includes three (3) class labels, the taxon for Exemplar Findings are labeled A, and Exemplar Illnesses are labeled B. Column C is reserved as the Instance Taxon presented by the patient during physical examination.

In the preferred implementation, scores are a function of taxonomic Novelty and Specificity. Taxonomic Novelty of a triggering verbiage is expressed as a surprisal. Verbiages that include common words are less novel. For example in ICD-10, the word combination 'PAIN' appearing 555 times and 'BACK." appearing 517 times, are together less novel than 'COCCYGODYNIA' which appears only twice. Thus the latter form of back pain is more novel than the former. The other variable, taxonomic Specificity, is the number of levels in a Taxon. In ICD-10, for example, this is easily computed as the number of extra digits appended to the base 3-digit code. In SNOMED CT, taxonomic specificity might be the number of codes in the post-coordinated representation of the Taxon. Depending on the step in this process, poset STEJCP may have been aggregated, in which case score S is further reduced (i.e., improved) in proportion to a Verbiage's frequency of mention. The lower the score, the more specific, novel, and frequent is the Verbiage P that triggered the rule.

The mappings generator 330 then derives association rules from the Artifact seeded by the Signature, from the signature generator, through adaptation of diffusion limited aggregation (DLA), to obtain a ranked list of terminology-to-code Mappings. Association rule mining generates Boolean product clauses in sum-of-products Expressions. STEP 102.

Traditionally, the antecedent and consequents of an association rule are drawn from the same set. As such, items on the antecedent are laterally associated with the item in the consequent. In the classic application of association rule mining to the Retail Grocery Industry, people who buy "bread and diapers" might also buy "beer". In accordance with the disclosed implementation, the possibly multiword verbiage in the antecedent typically denoting signs and symptoms instead abstract up to the Taxon in the consequent typically denoting some diagnosis. For example, the finding of "increased intraocular pressure" could abstract up to ICD-10 Taxon H40.0 for "suspected glaucoma". Other findings could abstract up to suspected glaucoma as well.

Taxons that have been previously discovered can appear in the antecedent along with added Verbiage that suggests a Taxon in the consequent for a more advanced stage or specific manifestation. This decoupling in time enables extending existing Encodings with notions of prior history or presence of underlying conditions or persistent risk factors. For example, the Taxon for "abnormal serum glucose" in the antecedent coupled with the finding of "dermal hyperesthesia" could map up to a Taxon in the consequent predicting early-stage type II diabetes mellitus.

Traditionally, association rules have been detected based on the frequency of both antecedent and consequent combined. Thus, only combinations of both sides having sufficient frequency are brought to the attention of the curating expert. As a result, an atypical presentation of an otherwise commonly occurring finding gleaned from patient data will be ignored. For example, the finding of "diabetic ketoacidosis" had traditionally been exclusively associated with type 1 diabetes. Only recently have we learned that in rare cases, this condition also presents with type 2 diabetes. In the disclosed implementation, interesting and novel Verbiage alone (i.e., the antecedent) is sufficient to trigger the attention of an expert. In that way, rare cases of diabetic ketoacidosis in patients with type II diabetes are not overlooked. This weakening of the traditional support requirement for association rules enables a curating clinical expert to specify new or emerging associations with what was once believed to be a well-studied illness. For example, not only can "diabetic ketoacidosis" be occasionally associated with Type II diabetes, but could furnish confirmatory diagnostic criteria for type 1 diabetes as well.

As background, diffusion limited aggregation (DLA) is ubiquitous in Nature, from growth patterns of axons and dendrites in our nervous systems, to veins of gold in the earth, to how the crack in your windshield spreads, to how transport networks evolve. In the first two examples involving nervous systems and gold mines, DLA is a process of accretion by which particles undergoing a random walk collide and stick (i.e., accrete) to existing structures. In the third example, drawn from the field of fracture mechanics, DLA is a process by which forces acting randomly on matter continue to splay fissures in a treelike manner outward from initial point of impact. The final example is drawn from the built environment. As infrastructures evolve, DLA is a process by which existing capacity is upgraded causing the need to build out peripheral capacity.

With that background regarding DLA, in the disclosed implementation, each proposed association rule contains a detected Verbiage in its entirety, in addition to a sufficiently 'interesting' combination of one or more additional words. In the realm of association rule mining, a word combination is said to be 'interesting' if it possesses sufficient 'support' (i.e., sample size) and statistical 'lift' and 'conviction'. By seeding proposed association rules with established Verbiages that might have appeared inside the ICD-10 Alphabetic List, these Verbiages grow by adding 'interesting' word combinations to them as well as augmenting, extending, or otherwise refining their Taxons. This random walk favors accreting Novel, Specific, and Frequently mentioned seeds to word combinations having high 'lift' and 'conviction'. This process mimics DLA.

Consider the following example for an early detection and intervention program for diabetic retinopathy:

"The first signs of nonproliferative (diabetic) retinopathy are capillary microaneurysms, dot and blot retinal hemorrhages, hard exudates, cotton-wool spots (soft exudates) along with pale or fatty deposits."

The initial Signature appearing in regular typeface seeds added Verbiages in bold as the following poset with columns for score, Taxon, and clause shows:

0.0207 H35.81 RETINA COTTON WOOL. SPOTS
0.0312 E11.329 E11.* RETINOPATH NONPROLIFERATIVE
0.0420 H35.04* RETINA MICROANEURYSM
0.0489 E11.319 E11.* RETINOPATH
0.0521 H35.02* RETINOPATH EXUDAT
0.0542 H35.89 EXUDAT RETINA
-.----H35.8A EXUDAT RETINA FATTY
-.----H35.8A EXUDAT RETINA HARD.
-.----H35.8A EXUDAT RETINA PALE.
-.----H35.81 EXUDAT RETINA SOFT.
0.0807 178.8 HEMORRHAG CAPILLARY
-.----H35.6A RETINA HEMORRHAG DOT.
-.----H35.6A RETINA HEMORRHAG BLOT.
0.1059 H35.6* RETINA HEMORRHAG
0.1587 H35.0* RETINOPATH
0.2171 E11.* DIABET
0.3560 R58 HEMORRHAG

In the example above, Taxon H35.8 grew out to the new Taxon H35.8A by further qualifying the exudates as fatty, hard, or pale. In this way, dictating physicians using these terms will have the proper Taxons detected. Taxon H35.8 also grew out to existing Taxon H35.81 by further qualifying the exudates as soft. Soft exudates have already been signified by cotton or wool spots as shown in the top-ranking table entry. Similarly, Taxon H35.6 grew out to H35.6A by further predicating it with morphology. As described below, a clinical expert must determine whether dot or blot hemorrhages are more predictive of non-traumatic and non-febrile etiology (i.e., diabetic retinopathy) than the types of retinal hemorrhage sustained through trauma or other means. In some cases, such an association might be well-known. In others, the expert must consult the primary source to referee this association. It should be noted that the score for these clauses are unassigned and will remain so until after the Extensions again get Encoded as described below.

As indicated above, a clinical expert may curate these Mappings, augmenting them to existing terminologies, taxonomies, and ontologies to create extended versions of each, known as Extensions. The extended clauses generated by the mapping generator are preferably curated by a clinical expert. In the example above, that clinician would be an Ophthalmologist. Once curated, these extended clauses are again Encoded to form Extensions to existing taxonomies and received by the exemplar generator 340. STEP 103.

In the preferred implementation, for each sentence in which codes in the Signature have been detected, present to the curating clinical expert a list that follows the typographic conventions found in the example above. Place checkboxes by each extended clause which by default remain unchecked, and provide the proper description for each Taxon found. Have the curating clinical expert check the appropriate boxes. Also enable the expert to edit the signature, including descriptions for any newly extended codes.

Typically, multiple sentence documents where each document concerns a specific illness will be curated by more than one clinical expert. For example, cross-disciplinary illnesses like diabetic retinopathy involve vascular mechanisms on the one hand and neurological mechanisms on the other [GABJ-11]. Each clinical specialty can contribute its own unique expertise in fingerprinting the same illness. In a preferred implementation, multiple specialists will be working on multiple illnesses in parallel. The common artifacts on which improvements are made will be the Taxonomies in their extended form (i.e., Extensions), while Exemplar signatures (i.e., combinations of Taxons) are more closely confined to each specialty. From time to time these Extensions get again Encoded into the data structure required by its Boolean Valuator. In the preferred implementation, that data structure is the hypergraph.

The changes are then entered to modify the clause set through a text editor, for example. The clause set (i.e., Extensions) is then re-compiled into the hypergraph and entered into the exemplar generator.

The exemplar generator receives the hypergraph and performs controlled indexing on the Artifact using the Extensions to generate the Exemplar code signature (i.e., fingerprint at Booking) for that disease, for example, and storing it for future matchups. STEP 104.

In the preferred implementation, the Exemplar signature code is a three-column relation ABX in which Findings Taxon A implies Illness Taxon B with Exemplar Distance X. For example, suppose the following entries from the diabetic retinopathy example were approved by the curating clinical expert and used by the exemplar generator:

A: B: X:
E11.* E11.319 0.2171
E11.319 E11.319 0.0489
E11.329 E11.319 0.0312
H35.0* E11.319 0.1587
H35.02* E11.319 0.0521
H35.04* E11.319 0.0420
H35.6* E11.319 0.1059
H35.81 E11.319 0.0191
H35.89 E11.319 0.0542
H35.8A E11.319 0.0103
178.8 E11.319 0.0807
R58 E11.319 0.3560

In this example, diabetes E11.* only weakly implies diabetic retinopathy E11.319 as evidenced by Exemplar Distance 0.2171. An even weaker association than this is the one for hemorrhage R58, with the even longer Exemplar Distance of 0.3560. Both of these have lower discriminatory power than the reflexive entry E11.319 E11.319 having Exemplar Distance 0.0489. (Reflexive entries have non-zero Distance—relaxing the Axiom of Identity of Indiscernibles required of strict Metric Spaces.) Consequently, entries having even shorter Distances might even be more pathognomonic for E11.319. In this example, fatty retinal exudates H35.8A having a distance of only 0.0103 is presumed to more closely indicate diabetic retinopathy, than simply saying so with the phrase: "DIABETIC RETINOPATHY" coded as an E11.319.

Since ABX is a poset, it is lexically ordered so that the same Finding A can be associated with any number of Illnesses B in the Exemplar signatures for all diseases. In a preferred implementation, this ordering increases the efficiency of matching.

Figure 2:
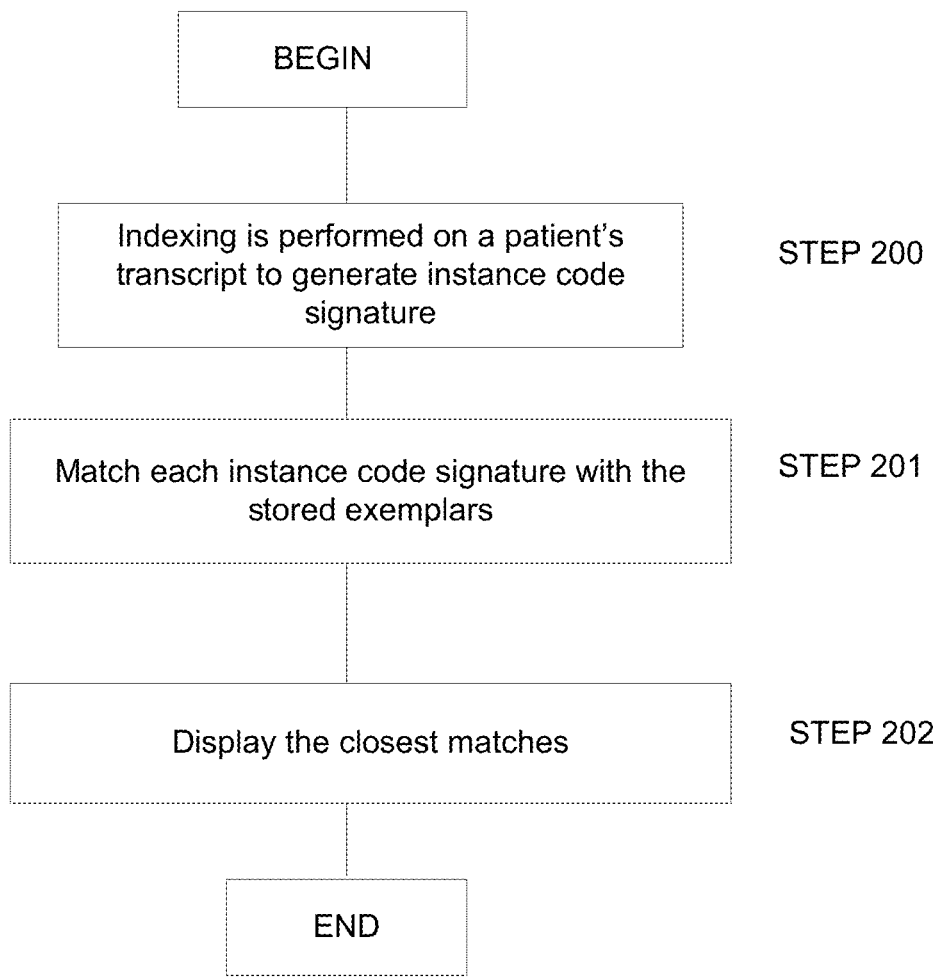
FIG. 2 is an example flow diagram of a method for matching the one or more exemplars with an instance in accordance with the present invention.

An example flow diagram of an implementation of a method for matching the exemplars to a patient instance is illustrated in FIG. 2. At patient presentation, the signature generator performs controlled indexing on the patient's Transcript using the Extensions to generate an Instance code signature (i.e., fingerprint at the Scene). STEP 200.

In the preferred implementation, the Instance signature poset CPY is a three-column table comprised of Instance Taxon C, Patient De-identifier P, and Instance Distance Y. Each patient's Instance signature is queued, concatenated, or pipelined behind Instance signatures of other patients that had been indexed and awaiting matchup. Preferably, patient de-identifiers are alpha numeric strings of 32 to 48 characters that signify a unique patient visit. A preferred implementation will not know the patient's identity, but instead communicates its results back to the EHR using an EHR-assigned de-identifier. As such, the EHR backs into a patient's identity given the de-identifier.

The matching engine receives the instance signature code and the exemplars, and matches each Instance to an Exemplar(s) on file, STEP 201, reporting the closest Matches. STEP 202. In accordance with the preferred implementation, Exemplars most closely matching an instance are those that minimize the square root of the sum of two numbers—an instance's Hits plus Misses. Hits are the sum of the products of Exemplar Distance X and Instance Distance Y for each Instance Taxon C that matches Finding Taxon A for Illness Taxon B. On the other hand, Misses are the sum of the Exemplar Distances X for Finding Taxons A and Illness Taxon B for which there are no matching Instance Taxons C.

It should be noted that Hits are the sum of products of numbers both of which are less than one, and Misses are the sum of products of one of these numbers multiplied by One. Thus, Hits are rewarded with closeness while Misses are penalized with distance. Note also that Instance signatures having more entries than usual are not being penalized, since some patients can present with multi-systemic illnesses. A Hit to Miss ratio may measure diagnostic adequacy of an instance.

Figure 4:
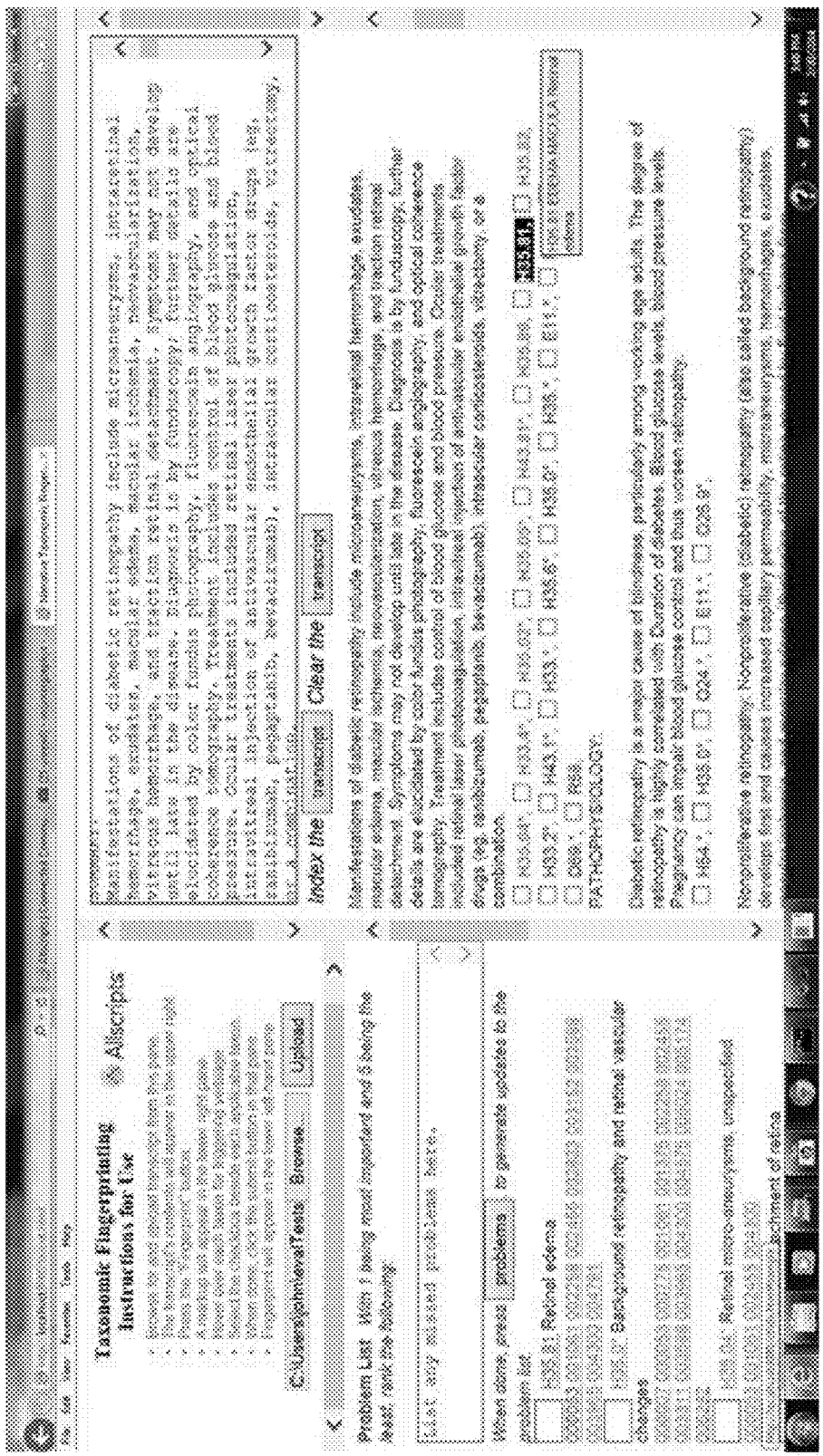
FIGS. 4, 5 and 6 are example screen shots of the implementation of the methods illustrated in FIGS. 2 and 3.
Figure 5:
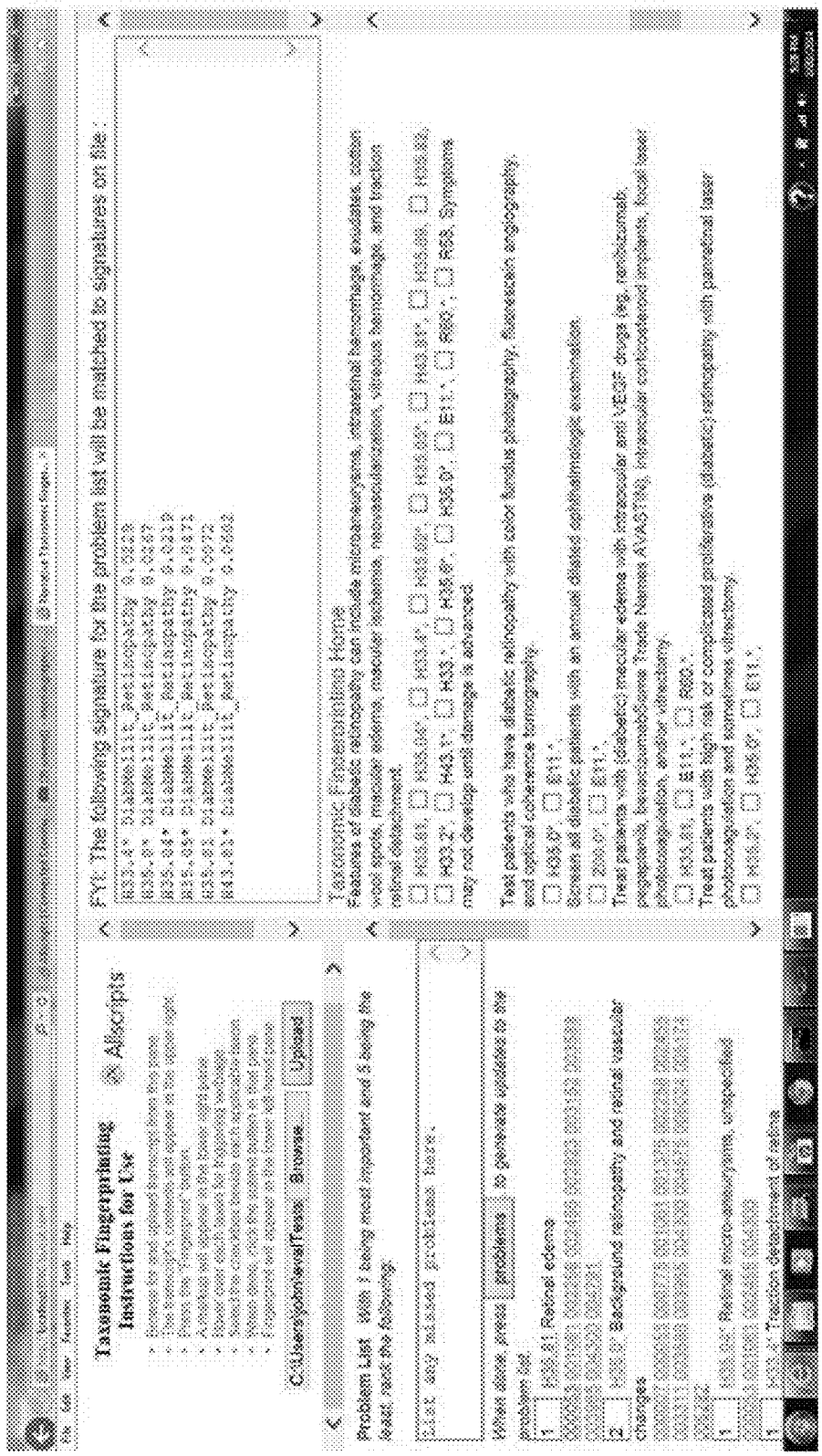
Figure 6:
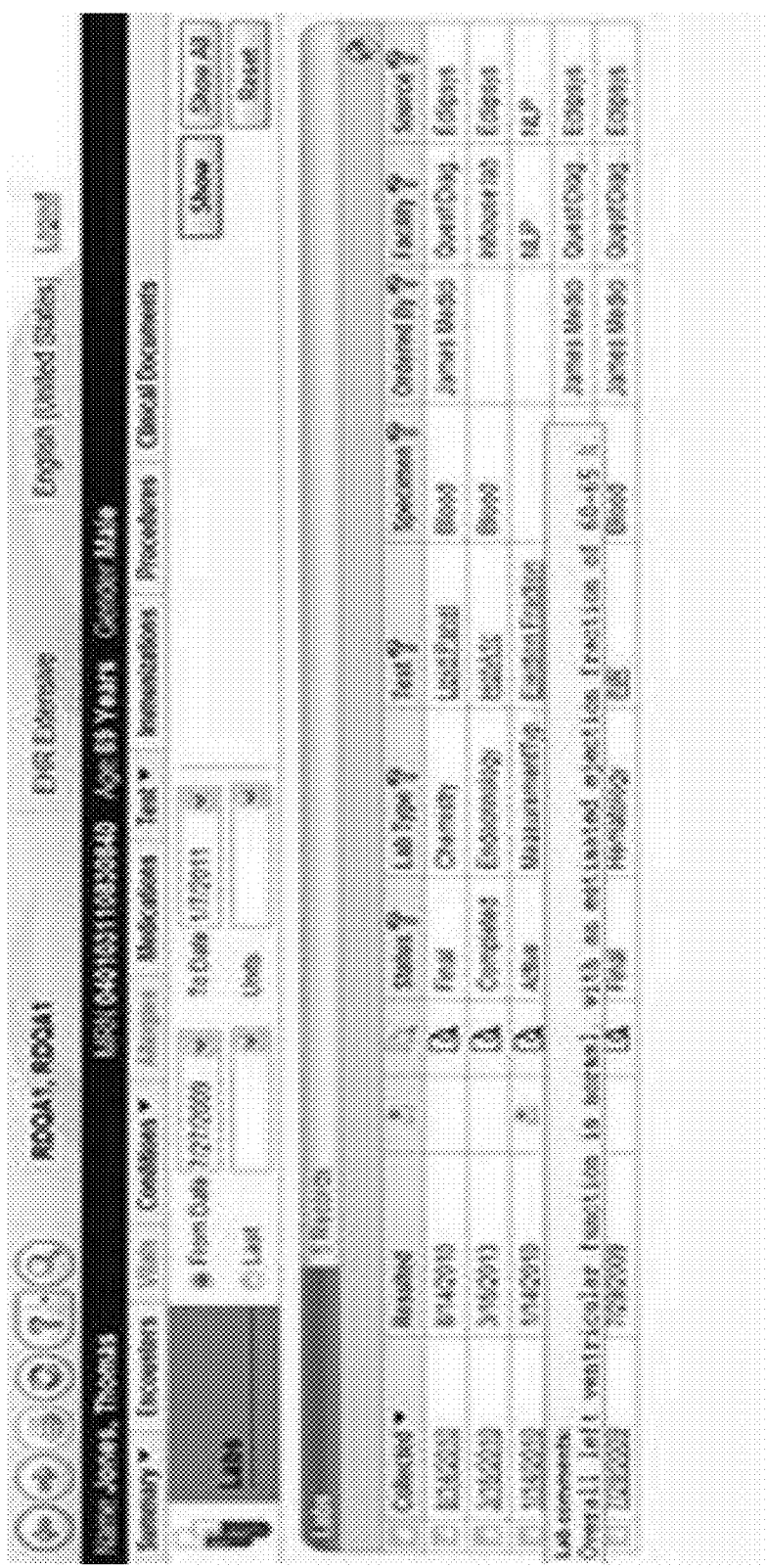

FIGS. 4, 5 and 6 are example screenshots of an implementation of the disclosed system and method. In FIG. 4, once the user selects a file to upload, the contents appear in the upper right pane. Pressing the code Transcript button activates the signature generator to index the file and derive an initial code signature. The detailed results are shown in the lower right pane. A sticky note is illustrated providing the user more information about the code, including triggering verbiage and description of the illness or finding.

Pressing the Problems button in that pane generates a candidate problem list shown in the lower left pane.

FIG. 5 illustrates the continued use case with the physician-user wishing to fingerprint diabetic retinopathy by placing priority numbers beside each code. Once the Problems button in that pane is pressed, a short list of the most salient codes that will characterize diabetic retinopathy are illustrated in the upper right hand window pane. A file, not shown, including this disease exemplar fingerprint is also produced. It should be noted that the fingerprint is a three-column table. The first contains the ICD-10 code, the second is the name of the perpetrator (diabetic retinopathy), and the third is a distance metric. This metric is based on four criteria: (i) taxonomic specificity (how long the code is), (ii) novelty (a surprisal that is an inverse function of frequencies of each word appearing in the taxonomy), (iii) frequency of mention (how often the ICD-10 code appears in the document in the lower right pane), and (iv) direct function of priority assigned to that finding by the user physician specializing in this particular pathology.

FIG. 6 is an illustration of an example screenshot of an application that utilizes the disclosed system and method. As Although the disclosed implementation has been exemplified relating to healthcare, it should be noted the disclosed method may be utilized in other industries as well, for example, retail.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method comprising:
   (I) electronically maintaining
      (a) a plurality of extensions to a medical taxonomy; and
      (b) a plurality of exemplar code signatures for illnesses, each exemplar code signature comprising a partially ordered set including one or more entries for which
         (i) a first column contains a findings taxon in the form of a clinical code,
         (ii) a second column contains an illness taxon implied by the respective findings taxon, the illness taxon being a clinical code for a disease, and
         (iii) a third column contains an exemplar distance indicating a strength of the implication of the respective illness taxon by the respective findings taxon;
      (c) wherein the plurality of exemplar code signatures includes an exemplar code signature for a first disease, the exemplar code signature for the first disease comprising a partially ordered set including one or more entries for which
         (i) a first column contains a findings taxon in the form of a clinical code,
         (ii) a second column contains an illness taxon implied by the respective findings taxon, the illness taxon being a clinical code for the first disease, and
         (iii) a third column contains an exemplar distance indicating a strength of the implication of the respective illness taxon by the respective findings taxon;
   (II) utilizing taxonomic fingerprinting to electronically determine that the first disease is a close match for a first patient's record by
      (a) performing controlled indexing on a patient transcript for the first patient using the extensions to obtain an instance code signature by
         (i) performing, by a text preprocessor on the patient transcript, text boundary detection, tokenization, and tagging;
         (ii) mapping, by a Boolean valuator, one or more instances of verbiage in the first content to one or more clinical taxons;
         (iii) generating the instance code signature which comprises a partially ordered set including one or more entries for which
            (A) a first column contains an instance taxon verbiage that was mapped to,
            (B) a second column contains a patient de-identifier, and
            (C) a third column contains an instance distance y for the respective instance taxon generated based on the mapping for the respective instance taxon;
      (b) electronically comparing the instance code signature to the plurality of maintained exemplar code signatures for illnesses, including the exemplar code signature for the first disease, by
         (i) for each respective exemplar code signature for a respective illness,
            (A) determining a hit value by summing the products of the exemplar distance and instance distance for each instance taxon that matches a finding taxon in that respective exemplar code signature,
            (B) determining a misses value by summing the exemplar distances for finding taxons and illness taxons for which there are no matching instance taxons,
            (C) calculating a closeness value representing a square root of the sum of the determined hit value and the determined misses value;
         (c) determining that the first exemplar code signature for the first disease is a closest match based on it having a lowest calculated respective closeness value; and
         (d) displaying, to a user via an electronic display associated with an electronic device, an indication that the first disease is the closest match for the first patient's record.

2. The method of claim 1, wherein the method further comprises, prior to utilizing taxonomic fingerprinting to electronically determine that the first disease is a close match for a first patient's record, generating the exemplar code signature for the first disease based on a first document.

3. The method of claim 2, wherein the first document comprises a medical article on the first disease.

4. The method of claim 2, wherein the method further comprises evaluating content of the first document for relevance.

5. The method of claim 2, wherein the method further comprises evaluating content of the first document for comprehensiveness.

6. The method of claim 2, wherein the method further comprises evaluating content of the first document for purity.

7. The method of claim 2, wherein the method further comprises automatically determining the admissibility of content of the first document.

8. The method of claim 1, wherein the method further comprises, prior to utilizing taxonomic fingerprinting to electronically determine that the first disease is a close match for a first patient's record, generating the exemplar code signature for the first disease based on content assimilated from a plurality of medical articles.

9. A method comprising:
   (I) electronically maintaining a plurality of extensions to a medical taxonomy;
   (II) electronically building a text artifact comprising first content by
      (a) crawling a source of medical literature,
      (b) automatically determining the admissibility of crawled medical articles, and
      (c) assimilating excerpts from medical articles determined to be admissible into the text artifact;
   (III) performing controlled indexing on the first content using the maintained plurality of extensions to obtain an exemplar code signature by
      (a) generating, for each of a plurality of respective problems, a distance metric indicating a strength of the implication of the first disease by the respective problem, each distance metric being generated based on
         (i) taxonomic specificity of the taxon for the respective problem, (ii) a surprisal that is an inverse function of frequencies of each word appearing in the medical taxonomy, (iii) a frequency of mention of the taxon for the respective problem in the first content;

(b) generating, by an exemplar generator utilizing the generated distance metrics, a first exemplar code signature for the first disease, the first exemplar code signature for the first disease comprising a partially ordered set including one or more entries for which (i) a first column contains a findings taxon in the form of a clinical code, (ii) a second column contains an illness taxon implied by the respective findings taxon, the illness taxon being a clinical code for the first disease, and (iii) a third column contains an exemplar distance indicating a strength of the implication of the respective illness taxon by the respective findings taxon, (iv) wherein one of the entries corresponds to the first taxon;

(IV) subsequently, utilizing taxonomic fingerprinting to electronically determine that the first disease is a close match for a first patient's record by (a) performing controlled indexing on a patient transcript for the first patient using the extensions to obtain an instance code signature by (i) performing, by a text preprocessor on the patient transcript, text boundary detection, tokenization, and tagging;

(ii) mapping, by a Boolean valuator, one or more instances of verbiage in the first content to one or more clinical taxons;

(iii) generating the instance code signature which comprises a partially ordered set including one or more entries for which (A) a first column contains an instance taxon verbiage that was mapped to, (B) a second column contains a patient de-identifier, and (C) a third column contains an instance distance y for the respective instance taxon generated based on the mapping for the respective instance taxon;

(b) electronically comparing the instance code signature to a plurality of maintained exemplar code signatures for illnesses, including the exemplar code signature for the first disease, by (i) for each respective exemplar code signature for a respective illness, (A) determine a hit value by summing the products of the exemplar distance and instance distance for each instance taxon that matches a finding taxon in that respective exemplar code signature, (B) determine a misses value by summing the exemplar distances for finding taxons and illness taxons for which there are no matching instance taxons, (C) calculating a closeness value representing a square root of the sum of the determined hit value and the determined misses value;

(c) determining that the first exemplar code signature for the first disease is a closest match based on it having a lowest calculated respective closeness value; and (d) displaying, to a user via an electronic display associated with an electronic device, an indication that the first disease is the closest match for the first patient's record.

10. The method of claim 9, wherein automatically determining the admissibility of crawled medical articles comprises evaluating relevance.

11. The method of claim 9, wherein automatically determining the admissibility of crawled medical articles comprises evaluating comprehensiveness.

12. The method of claim 9, wherein automatically determining the admissibility of crawled medical articles comprises evaluating purity.

13. The method of claim 9, wherein the crawled medical articles comprises articles emphasizing pathophysiology over treatment.

14. The method of claim 9, wherein the crawled medical articles comprises an article discussing signs.

15. The method of claim 9, wherein the crawled medical articles comprises an article discussing symptoms.

16. The method of claim 9, wherein the crawled medical articles comprises an article discussing etiologies.

17. The method of claim 9, wherein the crawled medical articles comprises an article discussing diagnoses.

* * * * *